Figure 1:
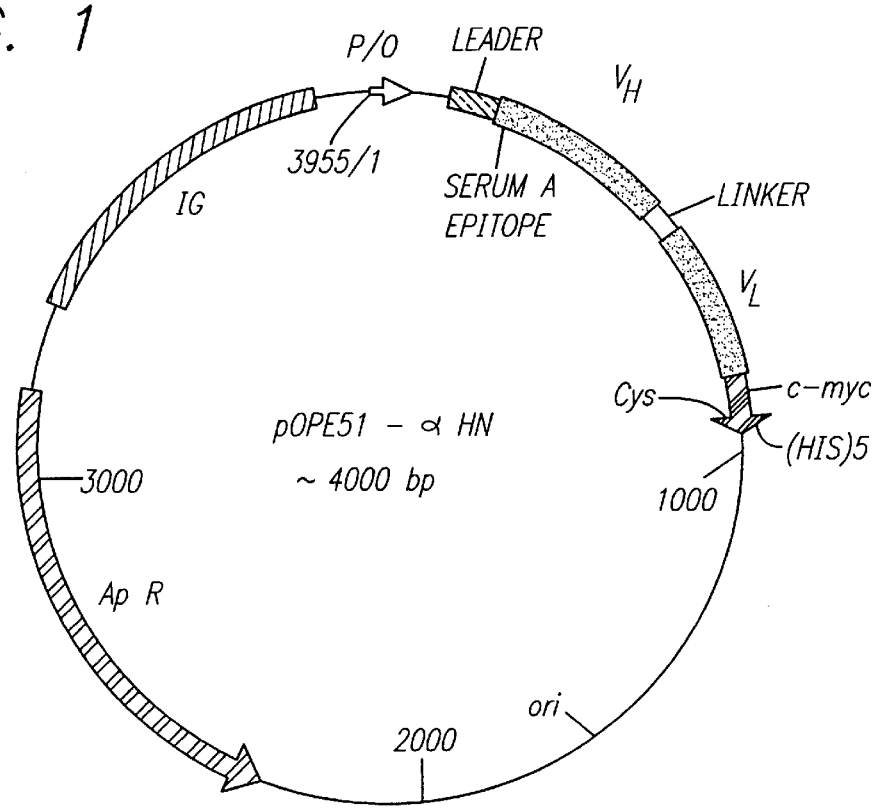

United States Patent [19]
Volker et al.

[11] Patent Number: 5,911,987
[45] Date of Patent: Jun. 15, 1999

[54] CELL SURFACE PROTEIN AND EFFECTOR CELL BONDING REAGENT

[75] Inventors: Schirrmacher Volker, Heidelberg; Khashayarsha Khazaie, Sandhausen; Claudia Haas, Schwaigern; Gerd Moldenhauer, Heidelberg; Melvyn Little, Neckargemünd; Stefan Dübel, Heidelberg; Frank Breitling, Heidelberg; Sergey Kipriyanov, Heidelberg; Stefanie Gotter, Heidelberg; Hans-Jürgen Rode, Heidelberg, all of Germany

[73] Assignee: Deutsches Krebsforschungszentrum Stiftung des Offentlichen Rechts, Heidelberg, Germany

[21] Appl. No.: 08/702,712

[22] PCT Filed: Mar. 7, 1995

[86] PCT No.: PCT/EP95/00843

§ 371 Date: Feb. 21, 1997

§ 102(e) Date: Feb. 21, 1997

[87] PCT Pub. No.: WO95/24490

PCT Pub. Date: Sep. 14, 1995

[30] Foreign Application Priority Data

Mar. 7, 1994 [DE] Germany .............. 44 07 538

[51] Int. Cl.⁶ .............. A61K 39/395; A61K 39/42; C07K 16/24
[52] U.S. Cl. .............. 424/136.1; 424/133.1; 424/145.1; 424/154.1; 424/159.1; 424/277.1; 530/387.3; 530/388.3; 530/388.22; 530/388.23
[58] Field of Search .............. 424/277.1, 133.1, 424/136.1, 145.1, 154.1, 159.1; 530/388.3, 388.22, 388.23, 387.3

[56] References Cited

FOREIGN PATENT DOCUMENTS 0 610 046  8/1994  WIPO .
WO 94/21798  9/1994  WIPO .

OTHER PUBLICATIONS

Bohlen et al., 1993, "Cytolysis Of Leukemic B–Cells By T–Cells Activated Via Two Bispecifc Antibodies," *Cancer Research* 53: 4310–4314.
Bohlen et al., 1993, "Lysis Of Malignant B Cells From Patients With B–Chronic Lymphocytic Leukemia By Autologous T Cells Activated With CD3 × CD19 Bispecific Antibodies In Combination With Bivalent CD28 Antibodies," *Blood* 82:1803–1812.
Ertel et al., 1993, "Viral Hemagglutinin Augments Peptide–Specific Cytotxic T Cell Responses," *European Journal of Immunology* 23:2592–2596.
Fanger et al., 1992, "Bispecific Antibodies," *Critical Reviews in Immunology* 12:101–124.

(List continued on next page.)

*Primary Examiner*—Toni R. Scheiner
*Attorney, Agent, or Firm*—Pennie & Edmonds LLP

[57] ABSTRACT

The present invention relates to a bonding reagent, which is characterized in that it comprises a first bonding component specific for the hemagglutinin-neuraminidase molecule of a Newcastle Disease Virus and a second bonding component specific for a costimulatorily acting molecule of an effector cell.

Furthermore, this invention concerns a process for the production of the bonding reagent as well as a vaccine containing the bonding reagent and inactivated tumor cells.

23 Claims, 2 Drawing Sheets

OTHER PUBLICATIONS

Nishimura et al., 1992, "Human c–erbB–2 Proto–Oncogene Product As A Target For Bispecific–Antibody–Directed Adoptive Tumor Immunotherapy," *International Journal of Cancer* 50:800–804.

Schirrmacher, 1993, "Active Specific Immunotherapy—A New Modality Of Cancer Treatment Involving The Patient's Own Immune System," *Onkologie* 16:290–296.

Azuma et al., 1993, "B70 antigen is a second ligand for CTLA–4 and CD28," *Nature 366:* 76–79.

Dübel et al., 1993, "A family of vectors for surface display and production of antibodies," *Gene 128*:97–101.

Freeman et al., 1993, "Cloning of B7–2: A CTLA–4 Counter–Receptor That Costimulates Human T Cell Proliferation," *Science 262*:909–911.

Iorio et al., 1986, "Genetic Variation within a Neutralizing Domain on the Haemagglutinin–Neuraminidase Glycoprotein of Newcastle Disease Virus," *J. gen. Virol. 67*:1393–1403.

Kurucs et al., 1993, "A bacterially expressed single–chain Fv construct from the 2B4 T–cell receptor," *Proc. Natl. Acad. Sci. USA 90*:3830–3834.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:1:

TGCATACATC ACCATCATCA T                          21

CELL SURFACE PROTEIN AND EFFECTOR CELL BONDING REAGENT

This is a national phase filing of the application No. PCT/EP95/00843, which was filed with the Patent Corporation Treaty on Mar. 7, 1995, and is entitled to priority of the German Patent Application P 44 07 538.3, filed Mar. 7, 1994.

I. FIELD OF THE INVENTION

The present invention relates to a bonding reagent, a process for the production thereof and a vaccine containing the bonding reagent.

II. BACKGROUND OF THE INVENTION

It is known that in the case of the active immunization the cells used often only show weak or no immunogenicity. This is found particularly when tumor cells are employed.

Experiments were made to increase the immunogenicity of cells. As in the use of oncolyzates obtained by Newcastle Disease Virus (referred to as NDV hereinafter), such experiments often failed to yield satisfactory results.

Thus, it is the object of this invention to provide a composition by which the immunogenicity of cells can be increased.

III. SUMMARY OF THE INVENTION

The present invention relates to a bonding reagent, which is characterized in that it comprises a first bonding component for a cell surface protein and a second bonding component for a costimulatorily acting molecule of an effector cell.

Furthermore, this invention concerns a process for the production of the bonding reagent as well as a vaccine containing the bonding reagent.

IV. BRIEF DESCRIPTION OF THE DRAWINGS

FIG. 1 shows a diagram of the expression plasmid pOPE51-αHN.

Abbreviations. $Ap^R$: gene encoding ampicillin resistance; bp: base pairs, c-myc: sequence coding for an epitope recognized by mAk 9E10; Cys: nucleotides which code for an individual cysteine residue; $(His)_5$: sequence coding for five C terminal histidine residues; IG: "intergenic" region of phage f1, leader: signal peptide sequence of the bacterial pectate lyase (pelB leader); linker: sequence coding for $(Gly_4Ser)_3$ linking $V_H$ and $V_L$; ori: origin of the DNA replication for ColE1; P/O: lac operon promoter/operator; $V_H$ and $V_L$: variable region of the heavy chain and light chain, respectively, of the anti-HN antibody.

Figure 2:
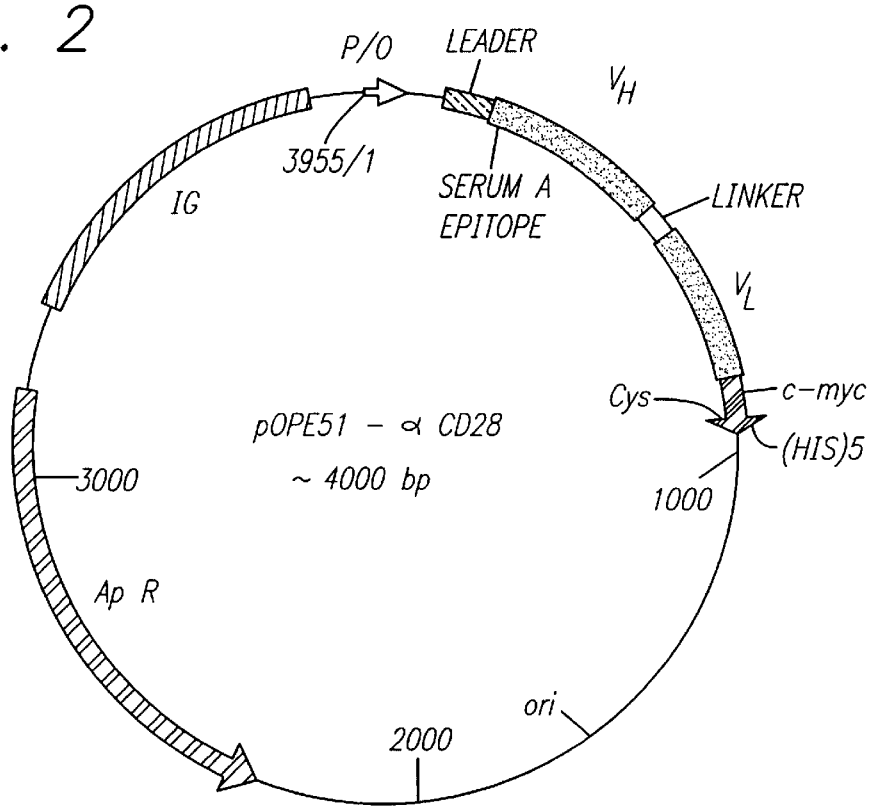

FIG. 2 shows a diagram of the expression plasmid pOPE51-αCD28.

Abbreviations. $Ap^R$: gene encoding ampicillin resistance; bp: base pairs; c-myc: sequence coding for an epitope which is recognized by mAk 9E10; Cys: nucleotides which code for an individual cysteine residue; $(His)_5$: sequence coding for five C terminal histidine residues; IG: "intergenic" region of phage f1, leader: signal peptide sequence of the bacterial pectate lyase (pelB leader); linker: sequence coding for $(Gly_4Ser)_3$ linking $V_H$ and $V_L$; ori: origin of the DNA replication for ColE1; P/O: lac operon promoter/operator; V and $V_L$: variable region of the heavy chain and light chain, respectively, of the anti-αCD28 antibody.

Figure 3:
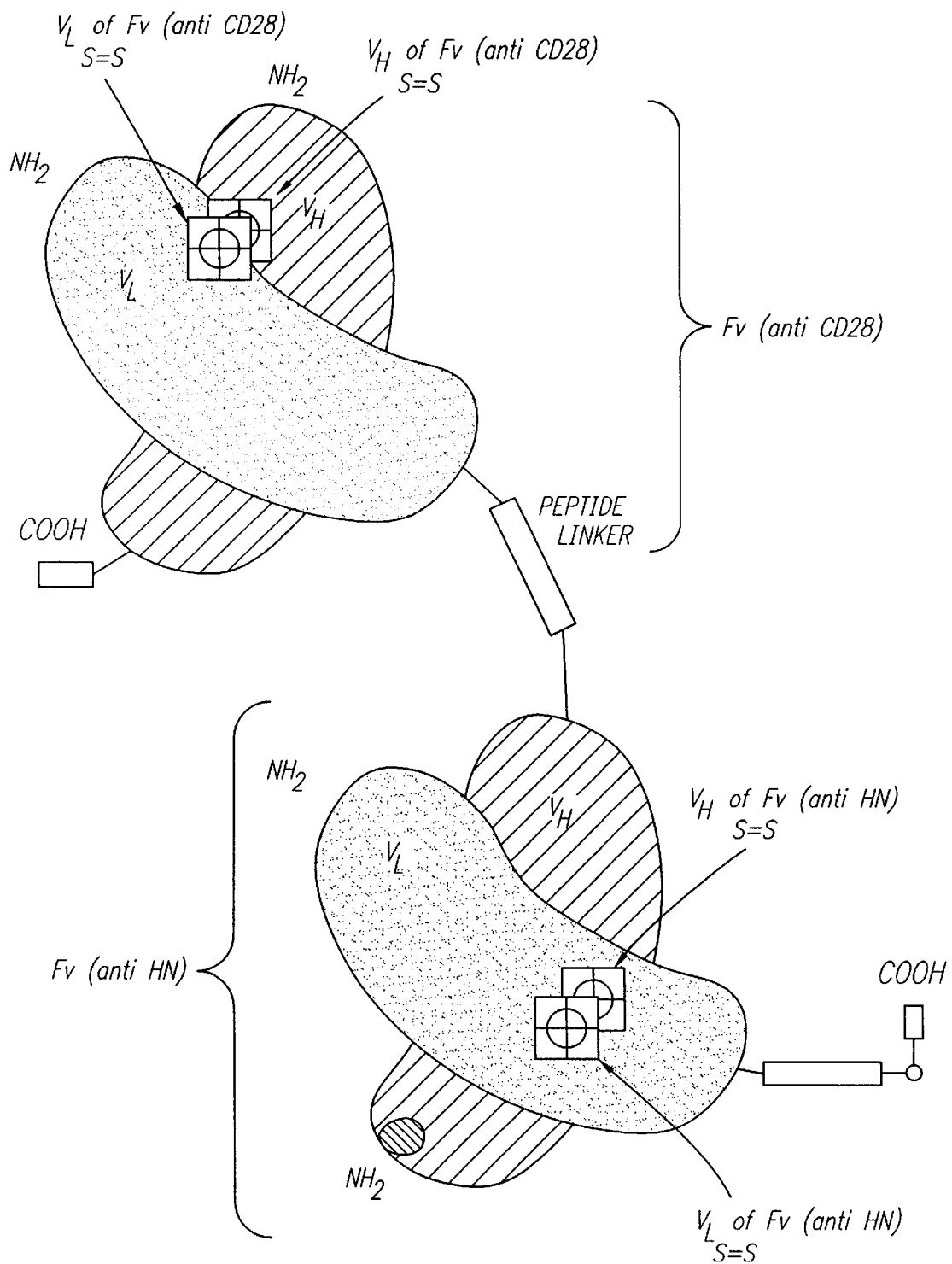

FIG. 3 shows a diagram of a bonding reagent according to the invention.

Abbreviations. anti HN: anti-HN antibody; anti CD28: anti-CD28 antibody; S=S: disulfide bridge.

V. DETAILED DESCRIPTION OF THE INVENTION

It is the objective of the subject invention to provide a composition by which the immunogenicity of cells can be increased.

According to the invention this is attained by providing a bonding reagent which is characterized in that it has a first bonding component for a cell surface protein and a second bonding component for a costimulatorily acting molecule of an effector cell.

The expression "first bonding component" comprises any compound which may bond to a cell surface protein, on the one hand, and to a second bonding component, on the other hand. The bond may be direct or indirect. Preferably, the compound is an antibody or a portion thereof which has a bonding domain. Such a portion is favorably a Fab', (Fab')$_2$, $F_v$ or $(F_v)_2$ fragment. The $F_v$ fragment of an anti-hemagglutininneuraminidase antibody has proved to be especially favorable.

The expression "cell surface protein" comprises any molecule which may be present on a cell surface. It may be a peptide or protein, for example, which originates from the cell as such, from a virus in the cell or from the expression of a DNA introduced into the cell. The "cell surface protein" is preferably a virus protein such as the hemagglutinin-neuraminidase molecule of NDV, the hemagglutinin molecule of influenza virus or the coat protein of HTLV-I and HIV, respectively, a growth factor receptor, an oncogene product such as v-Erb B2, an adhesion molecule, an antibody such as an antibody directed against hapten 2-phenyloxazole-5-one, or streptavidin (avidin) and a portion thereof, respectively. It has proved to be especially favorable for the cell surface protein to be a virus protein of NDV, the hemagglutinin-neuraminidase molecule of NDV having to be mentioned above all.

The expression "second bonding component" comprises any compound which may bond to a first bonding component, on the one hand, and to a costimulatorily acting molecule of an effector cell, on the other hand. The bond may be direct or indirect. The compound is preferably an antibody or a portion thereof which has a bonding domain. Such a portion is favorable a Fab', (Fab')$_2$, $F_v$ or $(F_v)_2$ fragment. The $F_v$ fragment of an anti-CD19, anti-CD20, anti-CD22 antibody, and anti-CD28 antibody, respectively, has proved to be especially favorable. In another preferred embodiment, the above compound is a B7 protein or a portion thereof. Azuma et al., 1993, Nature 366:76; Freeman et al., 1993, Science 262:909. It has proved to be especially favorable when such a portion does not comprise the membrane-bound domain. Furthermore, it is advantageous for the compound to be a lymphokine, interferon or interleukin.

The expression "effector cell" comprises any cell taking part in an immune reaction. It is preferably a T cell.

The expression "costimulatorily acting molecule" comprises any molecule of an effector cell, which by bonding or in another way can be induced to stimulate the effector cell.

Such a molecule may be a receptor, for example. In the case of a T cell, particularly the receptors CD2-, CD3-, CD19-, CD20-, CD22, CD26, CD28, and CTLA-4 as well as HSA (heat stable antigen) offer themselves as being favorable for the invention. In this connection, the receptor CD28 has to be emphasized above all.

In an above bonding reagent, the two bonding components may be connected directly or indirectly with each other. In the latter case, this may be effected via a complex, consisting, e.g., of streptavidin (avidin) as well as biotin and S protein as well as S peptide of the pancreatic ribonuclease A, respectively. For this purpose, one of the two bonding components includes streptavidin (avidin) and S protein or a portion thereof, respectively, and the other bonding component includes biotin and S peptide or a portion thereof, respectively. A person skilled in the art is familiar with processes serving for linking the constituents of the individual complexes to the bonding components and reacting them with one another so as to form the complexes. Bonding reagents in which the bonding components are bonding indirectly with one another are preferred.

Furthermore, bonding reagents are preferred in which one or both bonding components contain groups which are suitable to develop intermolecular disulfide bridges, i.e., disulfide bridges between bonding components of differing bonding reagents. Thus, e.g., bonding reagents which bond different, costimulatorily acting molecules can be bonding while linked to a single cell surface protein. In many cases, this proves to be especially favorable to increase the immunogenicity of cells.

The above bonding reagents may be produced according to conventional processes. A process comprising the following steps is favorable:

(a) insertion of a DNA encoding a first bonding component in an expression vector, expression of the DNA, isolation of the expression product and the purification thereof, (b) insertion of a DNA encoding a second bonding component in an expression vector, expression of the DNA, isolation of the expression product and the purification thereof, (c) linkage of the expression product of (a) with that of (b) as usual.

In steps (a) and (b), a first bonding component and a second bonding component, respectively, are produced by conventional DNA recombination techniques. The person skilled in the art is familiar with systems which can be used for the expression if the individual bonding components. He knows vectors, expression control elements and cells which can be used for this purpose. It has proved be to favorable to provide both bonding components as $F_v$ fragments of antibodies. Reference is made to the production of the $F_v$ fragment of an anti-hemagglutinin-neuraminidase antibody and the $F_{vm}$ fragment of an anti-CD28 antibody by way of example. The expression plasmids pOPE51-αHN and pOPE51-αCD28, respectively, are constructed for this purpose. See, Example 1, infra.

The expression plasmids pOPE51-αHN and pOPE51-αCD28 belong to the present invention.

In addition, the person skilled in the art is familiar with processes of purifying the resulting bonding components. Reference is made to the purification of the $F_v$-αHN fragment and the $F_v$-αCD28 fragment in below Example 2 by way of example.

In step (c), the bonding component of (a) is linked with that of (b). The person skilled int he art is familiar with processes usable for this purpose. He knows ones serving for direct and indirect linkages, e.g., via a streptavidin (avidin)/biotin or S protein/S peptide complex. Reference is made to the linkage of the $F_v$-αHN fragment with the $F_v$-αCD28 fragment in below Example 3 by way of example.

Another process has proved to be favorable to produce an above bonding reagent, e.g., one whose bonding components are $F_v$ fragment of differing specificities (specificity A; specificity B). In this process, the $F_v$ fragments are produced by combining their particular, partially individually expressed, $V_H$ and $V_L$ domains. For this purpose, groups which are suitable to develop disulfide bridges, e.g., cysteines, are introduced into the domains in such a way that predominantly $V_H$ and $V_L$ domains of one specificity are combined with one another.

In particular, two expression plasmids compatible with each other are used, by which the following constructs can simultaneously be expressed in a host, e.g., E. coli:

(a) a $V_H$ domain of a specificity A antibody, bound via a peptide linker of, e.g., 18 amino acids with the $V_L$ domain of a specificity B antibody;

(b) a free $V_H$ domain of a specificity B antibody; and (c) a free VL domain of a specificity A antibody.

Combinations of $V_H$ and $V_L$ domains are obtained. By the development of disulfide bridges these are predominantly combinations of the $V_H$ and $V_L$ domains of a specificity A and those of the $V_H$ and $V_L$ domains of specificity B. See, FIG. 3.

According to the invention a vaccine having inactivated cells is also provided, which is characterized in that one or more bonding reagents are bound to a cell surface protein. Such a vaccine preferably includes tumor cells which may originate from tumors removed in an operation or from an established cell line.

The (tumor) cells may be virus-modified Lysates of (tumor) cells, obtained by viruses, may also be present. NDV from virus is used advantageously. It has proved to be favorable for the bonding reagent or bonding reagents to be directed against a virus protein of NDV, particularly the hemagglutinin-neuraminidase molecule. Reference is made to the production of the tumor vaccines of below Example 4 by way of example.

The (tumor) cells may also be modified by the expression of a DNA introduced thereinto and encoding, e.g., streptavidin (avidin) or an antibody such as an antibody directed against the hapten 2-phenyloxazole-5-one. It has proved to be favorable for the bonding reagent or bonding reagents to be biotinylated in the case of streptavidin (avidin), whereas in the case of the antibody they contain the hapten 2-phenyloxazole-5-one.

By means of the bonding reagents according to the invention, which are to be attached to (tumor) cells, it is possible to transmit signals to costimulatorily acting molecules, e.g., receptors, of effector cells. Thus, effector cells do not only receive the signal transmitted by an antigen of (tumor) cells but are also costimulated. Therefore, the bonding reagents according to the invention are perfectly suitable to increase the immunogenicity of cells, particularly tumor cells. They represent a great improvement in the active immunization.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1: Construction Of The Expression Plasmids pOPE51-αHN And pO9PE51-αCD28

(A) Contruction of pO9E51-αHN

The vector pOPE40 was used as the starting material. Dubel et al., 1993, *Gene* 128:97. It contains a DNA encoding the $F_v$ fragment ($V_H + V_L$) of an anti-lysozyme antibody. The DNA for $V_H$ is linked with that for $V_L$ via a linker. The DNA of the above fragment is followed in the 3' direction by a DNA encoding an epitope of the monoclonal antibody 9E10 on the myc gene product.

For the production of pOPEE51-αHN, the DNA sequence TGC ATA CAT CAC CAT CAT CAT (SEQ ID NO:1) was inserted at the 3' end of the above myc DNA of pOPE40. By means of this DNA encoding the amino acid sequence Cys Ile His His His His His, the codon for the amino acid Asn was replaced at the 3' end of the myc DNA. Furthermore, the restriction sites BssHII and EcoRI were removed in the linker between $V_H$ and $V_L$. Moreover, three restriction sites, namely NcoI (nt. 76–81), MlnI (nt. 579–584) and NotI (nt. 910–917) were inserted in the vector portion. The expression plasmid pOPE51-αLys was obtained.

Finally, the DNA of the above $F_v$ fragment ($V_H$: PvuII-HindIII fragment; $V_L$: EcoRV-BamHI fragment) was replaced by that for the $F_v$ fragment ($V_H$: PvuII-HindIII fragment; $V_L$: EcoR$_V$-BamHI fragment) of an anti-hemagglutinin-neuraminidase antibody in this expression plasmid. The DNA of the latter fragment is referred to below as $F_v$-αHN DNA. The DNA for $V_H$ and $V_L$ of this fragment was obtained from the cDNA of a hybridoma cell line by means of conventional PCR technique. Iorio et al., 1986, *J. Gen. Virol.* 67:1393.

The expression plasmid pOPE51-αHN (FIG. 1) was obtained.

(B) Construction of pOPE51-αCD28

The construction of pOPE51-αCD28 was carried out on the basis of pOPE51-αLys as described under (A) for pOPE51-αHN. The DNA encoding the $F_V$ fragment ($V_H + V_L$) of an anti-CD28 antibody was obtained from the cDNA of a hybridoma cell line by means of conventional PCR technique. van Lier et al., in: Leucocyte Typing IV, Oxford University Press (1989), 353. The DNA of this fragment is referred to below as $F_v$-αCD28 DNA.

The resulting expression plasmid pOPE51-αCD28 is shown in FIG. 2.

B. Example 2: Expression Of The $F_V$-αHN And $F_V$-αCD28 DNA As Well Purification Of The Expression Products ($F_V$-αHN and $F_V$-αCD28 Fragments)

(A) Expression of the $F_V$-αHN DNA and purification of the expression product ($F_V$-αHN fragment)

*E. coli* JM109 cells were transformed as usual with the expression plasmid pOPE51-αHN and cultivated in 2 1 of LB medium at 30° C. up to an $OD_{600}$ of 0.7. Isopropyl-β-thiogalactoside (IPTG) was added up to a final concentration of 20 μm. The cells were incubated at room temperature for 3 h and then collected by centrifugation (4.500 g, 4° C., 15 min). The cells were suspended in 1/50 of the original volume in 0.1 M sodium acetate, pH 5.5, 10 mM EDTA, 1 mM phenylmethylsulfonylfluoride (PMSF) at 0C. Lysozyme was added up to a final concentration of 1 mg/ml. After 30 minutes of incubation on ice accompanied by slight shaking, the soluble cell plasma proteins were removed by centrifugation (30.000 g, 4° C., 30 min). The cell pellets were resuspended in 1/40 of the original volume in 30 mM sodium phosphate, 0.3 M NaCl, 1 mM PMSF, pH 7.0, and lyzed by sonication. Then centrifugation was carried out (30.000 g, 30 min, 4° C.) so as to remove soluble cytoplasm proteins.

The pellets were suspended in the same volume in 3 M urea, 25 mM Tris-HCl, 10 mM EDTA, pH 7.0, and the soluble proteins were removed by centrifugation as described above. Inclusion bodies were resuspended in 1/40 of the original volume in 6 M GuHCl, 0.1 M Tris-HCl, 10 mM EDTA, pH 7.0. The mixture was centrifuged again (30.000 g, 30 min, 4° C.) and the supernatant was dialyzed against 6 M urea, 25 mM Tris-HCl, pH 7.0. Imidazole was added up to a final concentration of 30 mM. The protein solution was placed on a chelating sepharose fast flow column loaded with $niCl_2$ and equilibrated with 6 M urea, 25 mM Tris-HCl and 50 mM imidazole, pH 7.0. The column was washed with 5 times the column volume of 6 M urea, 25 mM Tris-HCl, 50 mM imidazole, pH 7.0. Bonded $F_V$-αHN fragments were eluted with 1.5 times the column volume of 6 M urea, 25 mM Tris-HCl, 250 mM imidazole, pH 7.0. Then an IMAC was carried out at room temperature. The eluted protein was dialyzed at 4° C. against 0.4 M L-arginine-HCl, 0.1 M Tris-HCl, 5 mM EDTA, pH 7.0, the concentrated using permeable collodion bags (retention capacity: 12.4 kDa) and thereafter supplied to a Superdex 75 HL26/60 column equilibrated with 0.4 M Larginine-HCl, 0.1 M Tris-HCl, 5 mM EDTA, pH 7.0. A size exclusion chromatography was carried out under conditions as described by Kurucz et al., 1993, *PNAS USA* 90:3830. For calibrating the column, a gel filtration calibration kit consisting of ribonuclease A (13.7 kDa), chymotrypsinogen A (25 kDa), ovalbumin (43 kDa) and bovine serum albumin (67 kDa) was used. The eluted fractions with the $F_V$-αHN fragment were collected and dialized against PBS (15 mM sodium phosphate, 0.15 m NaCl, pH 7.0). The protein concentrations were determined as usual.

(B) Expression of the $F_V$-αCD28 DNA and purification of the expression Product ($F_V$-αCD28 fragment The expression of the $F_V$-αCD28 DNA and the purification of the $F_V$-αCD28 fragment were carried out as described under (A) for $F_V$-αHN DNA (fragment).

C. Example 3: Linkage Of The $F_V$-αHN Fragment With The $F_v$-αCD28 fragment 10 mg of the $F_V$-αHN fragment (1 mg/ml) of Example 2(A) were incubated with a hundredfold excess of the bifunctional sulfhydryl compound bismaleimidohexane (BMH, 1 mM) at room temperature for 30 min. Then, residues of the sulfhydryl compound were removed by dialysis against PBS. Thereafter, the $F_V$-αCD28 fragment of Example 2(B) was added in equimolar amount. The mixture was incubated at room temperature for 30 min so as to obtain the bonding reagent $F_V$-αHN/$F_V$-αCD28 according to the invention.

D. Example 4: Production of a tumor vaccine

Fat and connective tissue of freshly operated tumor tissue were removed as usual. The tumor tissue was cut into small pieces and incubated with 40 ml of an enzyme cocktail (collagenase 0.32 mg/ml, DNase 0.535 mg/ml and hyaluronidase 0.535 mg/ml in HBSS) with stirring at 37° C. for 1 h. The resulting cell suspension was drained through a common nylon net. In the case of "very hard" tumors, tissue residues or remainders were incubated with the above enzyme cocktail (40 ml) a second time and filtered. All suspensions were combined, filled with HBSS to give 50 ml and centrifuged at 1.200 revolutions per minute for 15 min. The supernatant was discarded and the pellet was resuspended in 10 ml of the above DNase solution and incubated at 37° C. for 10 min. The suspension was filled with HBSS to give 50 ml and centrifuged at 1.300 revolutions per minute for 10 min. The pellet was resuspended in 10 ml of HBSS and the cells were counted in a cell (Neubauer type) by means of trypan blue. When more than $6\times10^7$ living tumor cells and a portion of non-tumor cells (lymphocytes and monocytes) of more than 50% of the total cells were present, another separation step was carried out to remove the lymphocytes and monocytes. 100 µl of dynabeads anti-CD2 (Pan-T), anti-CD19 (Pan-B) and antiCD14 (Pan-monocytes) each were filled in tubes and washed three times with 7 ml of cold HBSS/HSA each. Cells resuspended in 2 ml of cold HBSS/HSA were added to these tubes, and the tubes were incubated on ice for 30 min. Magnetic beads were removed by a magnet and the cell suspension was withdrawn, filled in tubes with 50 ml HBSS and centrifuged at 1.300 revolutions per minute for 10 min. The supernatant was discarded, the pellet was resuspended in 50 ml HBSS and then centrifuged at 1.300 revolutions per minute for 10 min.

The resulting cell pellet was resuspended in HBSS, $1\times10^7$ cells having been taken up in 0.5 ml HBSS. About 0.5 ml of the resulting cell suspension was filled in prepared tubes which can be frozen. About 0.5 ml of double freezing medium on ice was added thereto, before the tubes which can be frozen were stored overnight at –70° C. and then kept in liquid nitrogen.

50 µl of the above cell suspension not provided with freezing medium were placed on ice for cytospin preparations and diluted 1:1 in each case with PBS in a dilution series. 50 µl of the above dilution series each were added to 6 Eppendorf cups having 50 µl of PBS/BSA each, and the cups were introduced into a cytospin apparatus. After 5 minutes of centrifugation at 1.000 revolutions per minute, the slides were fixed in air with 100% of methanol for 1 min. Then, staining took place according to the known method by Pappenheim. Thereafter, the cells were investigated by means of light microscopy as to their tumor cell content. When the tumor cell content was less than 50%, the above cell suspension was not used as a vaccine.

When the tumor cell content was more than 50%, the above cell suspension was thawed at 37° C., placed in a tube and filled with PBS to give 14 ml. After 10 minutes of centrifugation at 1.300 revolutions per minute, the supernatant was discarded. The pellet was resuspended in 100 µl of PBS, placed in tubes which can be frozen and admixed with 30 ml of NDS suspension (concentration 1.000 HAU/ml). Then, 30 minutes of incubation took place at 37° C., slight shaking taking place after 15 minutes. Careful washing followed the incubation, before an aliquot of tumor cells ($5\times10^6$ vital tumor cells) was incubated with about 5 µg of protein of the bonding reagent of Example 3 according to the invention at 37° C. for 30 min. Then, the cell suspension was irradiated with 200 Gy. The cell suspension was stored on ice up to its injection, then it was drawn up in a syringe and injected intradermally using a 0.9×40 ml cannula.

All references cited within the body of the instant specification are hereby incorporated by reference in their entirety.

---

---

We claim:

1. A bonding reagent, having a first bonding component binding to the hemagglutirnin-neuraminidase molecule of a Newcastle Disease Virus or binding to an antibody directed against hapten 2-phenyloxazole-5-one, and a second bonding component binding to a costimulatorily acting molecule of an effector cell.

2. The bonding reagent of claim 1, wherein said first bonding component is an antibody or a portion thereof which has a bonding domain.

3. The bonding reagent of claim 2, wherein said portion of the antibody is a Fab', $(Fab')_2$, $F_V$ or $(F_V)_2$ fragment.

4. The bonding reagent of claim 1, wherein said second bonding component is an antibody or a portion thereof which has a bonding domain.

5. The bonding reagent of claim 4, wherein said portion of the antibody is a Fab', $(Fab')_2$, $F_V$ or $(F_V)_2$ fragment.

6. The bonding reagent of claim 1, wherein said second bonding component is a B7 protein or a portion thereof.

7. The bonding reagent of claim 6, wherein said B7 portion does not comprise the membrane-bound domain.

8. The bonding reagent of claim 1, wherein said effector cell is a T cell.

9. The bonding reagent of claim 8, wherein said costimulatorily acting molecule is selected from the group consisting of CD2, CD3, CD19, CD20, CD22, CD26, CD28, CTLA-4 receptor and MHSA.

10. The bonding reagent of claim 1, wherein said bonding components are linked with one another via a complex.

11. The bonding reagent of claim 10, wherein said complex consists of streptavidin or avidin and biotin.

12. The bonding reagent of claim 10, wherein said complex consists of S protein and S peptide.

13. A process for the production of the bonding reagent of claim 1, comprising:
(a) insertion of a DNA encoding a first bonding component in an expression vector, expression of the DNA, isolation of the expression product and the purification thereof;
(b) insertion of a DNA encoding a second bonding component in an expression vector, expression of the DNA, isolation of the expression product and the purification thereof, and
(c) linkage of the expression product of (a) with that of (b).

14. A vaccine having inactivated cells, wherein at least one bonding reagent of claim 1 is bound to a cell surface protein.

15. The vaccine of claim 14, wherein said cells are tumor cells.

16. The vaccine of claim 15, wherein said tumor cells originate from tumors removed in an operation.

17. The vaccine of claim 16, wherein said tumor cells originate from an established cell line.

18. The vaccine of claim 14, wherein said cell surface protein is an antibody.

19. The vaccine of claim 18, wherein said antibody is directed against hapten 2-phenyloxazole-5-one.

20. The vaccine of claim 14, wherein said cells are virus-modified.

21. The vaccine of claim 20, wherein said virus is a Newcastle Disease Virus.

22. The vaccine of claim 21, wherein said cell surface protein is hemagglutinin-neuraminidase molecule.

23. A process for the production of the bonding reagent of claim 1, comprising:
(a) generating a first bonding component, comprising:
    (i) providing an expression plasmid comprising a nucleic acid encoding a first bonding component of the bonding agent of claim 1;
    (ii) expressing said nucleic acid encoding said first bonding component; and
    (iii) isolating said first bonding component;
(b) generating a second bonding component, comprising:
    (i) providing an expression plasmid comprising a nucleic acid encoding a second bonding component of the bonding agent of claim 1;
    (ii) expressing said nucleic acid encoding said second bonding component; and
    (iii) isolating said second bonding component; and
(c) linking said first bonding component of (a) with said bonding component of (b) so that the bonding agent is generated.

* * * * *

UNITED STATES PATENT AND TRADEMARK OFFICE
CERTIFICATE OF CORRECTION

PATENT NO. : 5,911,987
DATED : June 15, 1999
INVENTOR(S) : Schirrmacher et al.

It is certified that error appears in the above-identified patent and that said Letters Patent is hereby corrected as shown below:

Title page,
After "United States Patent [19]," please change "Volker et al." to -- Schirrmacher et al. --.
After item "[75] Inventors," please change the designation of the first named inventor from Schirrmacher Volker, Heidelberg;" to -- Volker Schirrmacher, Heidelberg; --.

Column 3,
Line 44, change "It has proved be to favorable" to -- It has proved to be favorable --.
Line 60, change "skilled int he art" to -- skilled in the art --.

Column 5,
Line 4, change "pO9PE51-αCD28" to -- pOPE51-αCD28 --.
Line 6, change "Construction of pO9E51-αHN" to -- Construction of pOPE51-αHN --.
Line 14, change "pOPEE51-αHN" to -- pOPE51-αHN --.
Line 50, change "DNA As Well Purification" to -- DNA As Well As Purifcation --.
Line 59, change "concentration of 20 $\mu$ m" to -- concentration of 20 $\mu$M --.
Line 63, change "at 0C" to -- at 0°C --.

Column 6,
Line 15, change "loaded with niCi$_2$" to -- NiCi$_2$ --.
Line 26, change "Larginine-HCi" to -- L-arginine-HCi --.
Line 35, change "0.15 m NaCi" to -- 0.15 M NaCi --.

UNITED STATES PATENT AND TRADEMARK OFFICE
CERTIFICATE OF CORRECTION

PATENT NO.   : 5,911,987
DATED        : June 15, 1999
INVENTOR(S)  : Schirrmacher et al.

It is certified that error appears in the above-identified patent and that said Letters Patent is hereby corrected as shown below:

Column 8,
Claim 1,
Change "hemagglutirnin-neuraminidase" to -- hemagglutinin-neuraminidase --.

Claim 9,
Change "and MHSA" to -- and HSA --.

Column 9,
Claim 17,
Change "The vaccine of claim 16" to -- The vaccine of claim 15 --.

Signed and Sealed this

Ninth Day of October, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 5,911,987
DATED : June 15, 1999
INVENTOR(S) : Schirrmacher et al.

It is certified that error appears in the above-identified patent and that said Letters Patent is hereby corrected as shown below:

Title page,
After "United States Patent [19]," please change "Volker et al." to -- Schirrmacher et al. --.
After item [75] Inventors," please change the designation of the first named inventor from Schirrmacher Volker, Heidelberg;" to -- Volker Schirrmacher, Heidelberg; --.

Column 3,
Line 44, change "It has proved to be to favorable" to -- It has proved to be favorable --.
Line 60, change "skilled int he art" to -- skilled in the art --.

Column 5,
Line 4, change "pO9PE51-αCD28" to -- pOPE51-αCD28 --.
Line 6, change "Construction of pO9E51-αHN" to -- Construction of pOPE51-αHN --.
Line 14, change "pOPEE51-αHN" to -- pOPE51-αHN --.
Line 50, change DNA As well Purification" to -- DNA As Well As Purification --.
Line 59, change "concentration of 20 μ m" to -- concentration of 20 μM --.
Line 63, change "at 0C" to -- at 0°C --.

Column 6,
Line 15, change "loaded with niCl$_2$" to -- NiCl$_2$ --.
Line 26, change "Larginine-HCl" to -- L-arginine-HCl --.
Line 35, change "0.15 m NaCl" to -- 0.15 M NaCl --.

Column 8, claim 1,
Change "hemagglutirnin-neuraminidase" to -- hemagglutinin-neuraminidase --.

Column 8, claim 9,
Change "and MHSA" to -- and HSA --.

UNITED STATES PATENT AND TRADEMARK OFFICE
CERTIFICATE OF CORRECTION

PATENT NO. : 5,911,987
DATED : June 15, 1999
INVENTOR(S) : Schirrmacher et al.

It is certified that error appears in the above-identified patent and that said Letters Patent is hereby corrected as shown below:

<u>Column 9, claim 17,</u>
Change "The vaccine of claim 16" to -- The vaccine of claim 15 --.

This certificate supersedes Certificate of Correction issued October 9, 2001.

Signed and Sealed this

Fifteenth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 5,911,987
DATED         : June 15, 1999
INVENTOR(S)   : Volker et al.

It is certified that error appears in the above-identified patent and that said Letters Patent is hereby corrected as shown below:

<u>Title page,</u>
Item [73], change the "Assignee" from Deutsches Krebsforschungszentrum Stiftung des Offentlichen Rechts, Heidelberg, Germany to -- Professor Dr. Volker Schirrmacher, Heidelberg, Germany; Professor Dr. Melvyn Little, Neckargemünd, Germany; and Dr. Hans-Jürgen Rode, Leimen/St. llgen, Germany --.

Signed and Sealed this

Twenty-fifth Day of June, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.   : 5,911,987
DATED        : June 15, 1999
INVENTOR(S)  : Schirrmacher et al.

Page 1 of 1

It is certified that error appears in the above-identified patent and that said Letters Patent is hereby corrected as shown below:

<u>Title page,</u>
Item [73], change the "Assignee" from Deutsches Krebsforschungszentrum Stiftung des Offentlichen Rechts, Heidelberg, Germany to -- Professor Dr. Volker Schirrmacher, Heidelberg, Germany; Professor Dr. Melvyn Little, Neckargemünd, Germany; and Dr. Hans-Jürgen Rode, Leimen/St. llgen, Germany --.

This certificates supersedes Certificate of Correction issued June 25, 2002.

Signed and Sealed this

Fourth Day of February, 2003

JAMES E. ROGAN
*Director of the United States Patent and Trademark Office*